US008481543B2

(12) United States Patent
Riscoe et al.

(10) Patent No.: US 8,481,543 B2
(45) Date of Patent: Jul. 9, 2013

(54) COMPOUNDS FOR TREATING PARASITIC DISEASE

(75) Inventors: Michael K. Riscoe, Tualatin, OR (US); Rolf W. Winter, Portland, OR (US); David J. Hinrichs, Lake Oswego, OR (US)

(73) Assignees: Oregon Health & Science University, Portland, OR (US); The United States of America as represented by the Department of Veterans Affairs, Washington, DC (US)

( * ) Notice: Subject to any disclaimer, the term of this patent is extended or adjusted under 35 U.S.C. 154(b) by 233 days.

(21) Appl. No.: 13/129,791

(22) PCT Filed: Nov. 17, 2009

(86) PCT No.: PCT/US2009/064811
§ 371 (c)(1),
(2), (4) Date: May 17, 2011

(87) PCT Pub. No.: WO2010/059633
PCT Pub. Date: May 27, 2010

(65) Prior Publication Data
US 2011/0251209 A1    Oct. 13, 2011

Related U.S. Application Data

(60) Provisional application No. 61/199,653, filed on Nov. 18, 2008.

(51) Int. Cl.
*A61K 31/497*    (2006.01)
*A61K 31/47*    (2006.01)
*C07D 215/38*    (2006.01)
*C07D 241/04*    (2006.01)

(52) U.S. Cl.
USPC ....... 514/252.11; 514/313; 544/357; 546/176

(58) Field of Classification Search
USPC .............. 514/252.11, 313; 546/176; 544/357
See application file for complete search history.

(56) References Cited

U.S. PATENT DOCUMENTS

| 2,233,970 | A | 3/1941 | Andersag |
| 3,173,918 | A | 3/1965 | Baget |
| 5,270,037 | A | 12/1993 | Bienzle |
| 5,596,002 | A | 1/1997 | Hofheinz et al. |
| 5,948,791 | A | 9/1999 | Hofheinz et al. |
| 7,371,778 | B2 | 5/2008 | Vennerstrom et al. |
| 2006/0014786 | A1 | 1/2006 | Raut |
| 2006/0074105 | A1 | 4/2006 | Ware, Jr. et al. |
| 2006/0270852 | A1 | 11/2006 | Yadav et al. |
| 2008/0188462 | A1 | 8/2008 | Peyton et al. |

FOREIGN PATENT DOCUMENTS

| WO | WO 95/35287 | 12/1995 |
| WO | WO 00/50404 | 8/2000 |
| WO | WO 02/072554 | 9/2002 |
| WO | WO 2006/088541 | 8/2006 |
| WO | WO 2007/045987 | 4/2007 |

OTHER PUBLICATIONS

De et al., "Aminoquinolines That Circumvent Resistance in *Plasmodium falciparum* In Vitro," *Am. J. Trop. Med. Hyg.*, 55(6):579-583, 1996.
Geary et al., "Effects of combinations of quinolone-containing antimalarials on *Plasmodium falciparum* in culture," *Annals of Tropical Medicine and Parasitology* 80(3):285-291, 1986.
Geary et al., "Lack of Cross-Resistance to 4-Aminoquinolines in Chloroquine-Resistant *Plasmodium falciparum* in vitro," *J. Parasitol.* 69(1):97-105, 1983.
O'Neill et al., "A Medicinal Chemistry Perspective on 4-Aminoquinoline Antimalarial Drugs," *Current Topics in Medicinal Chemistry* 6:479-507, 2006.
O'Neill et al., "Isoquine and Related Amodiaquine Analogues: A New Generation of Improved 4-Aminoquinoline Antimalarials," *J. Med. Chem.* 46:4933-4945, 2003 (Published online Sep. 30, 2003).
Ridley et al., "4-Aminoquinoline Analogs of Chloroquine with Shortened Side Chains Retain Activity against Chloroquine-Resistant *Plasmodium falciparum*," *Antimicrobial Agents and Chemotherapy* 40(8):1846-1854, Aug. 1996.
Stocks et al., "Novel Short Chain Chloroquine Analogues Retain Activity Against Chloroquine Resistant K1 *Plasmodium falciparum*," *J. Med. Chem.* 45:4975-4983, 2002 (Published online Oct. 3, 2002).
White et al., "Averting a malaria disaster," *The Lancet* 353:1965-1967, 1999.
International Search Report from International Application No. PCT/US2009/064811 dated Jul. 30, 2010.
Written Opinion of the International Searching Authority from International Application No. PCT/US2009/064811 dated Jul. 30, 2010.
Pub Chem Database AC1MXUPJ Compound Summary (CID 3796389), Create Date Sep. 11, 2005.

*Primary Examiner* — Kristin Bianchi
(74) *Attorney, Agent, or Firm* — Klarquist Sparkman, LLP

(57) ABSTRACT

A compound, particularly an antimalarial compound, according to formula I:

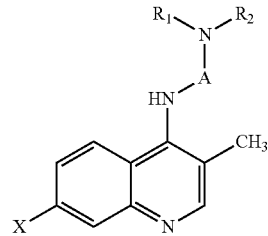

or a pharmaceutically acceptable salt thereof, wherein:
X is an electron-withdrawing group;
A is an optionally substituted alkanediyl or an optionally substituted cycloalkanediyl that includes 2 to 5 carbon atoms; and
$R_1$ and $R_2$ are each individually H, tert-butyl, isopropyl, or optionally substituted cycloalkyl.

35 Claims, 2 Drawing Sheets

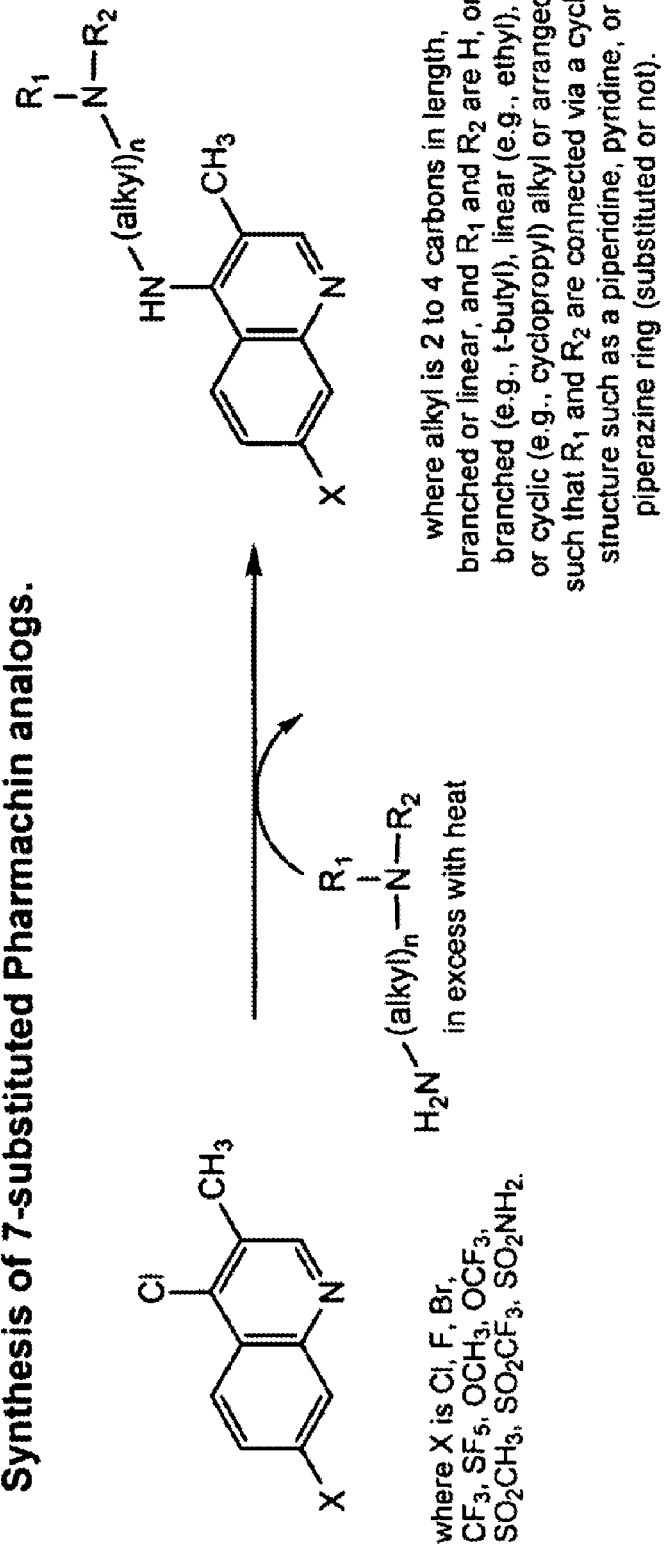

FIG. 1

Synthesis of 7-substituted Pharmachin analogs.

where X is Cl, F, Br, $CF_3$, $SF_5$, $OCH_3$, $OCF_3$, $SO_2CH_3$, $SO_2CF_3$, $SO_2NH_2$.

where alkyl is 2 to 4 carbons in length, branched or linear, and $R_1$ and $R_2$ are H, or branched (e.g., t-butyl), linear (e.g., ethyl), or cyclic (e.g., cyclopropyl) alkyl or arranged such that $R_1$ and $R_2$ are connected via a cyclic structure such as a piperidine, pyridine, or piperazine ring (substituted or not).

*Note: Synthesis of X-substituted 4-chloro-3-methyl-quinolines is by the method of Andersag et al. and modified by substitution of the appropriate meta-aniline in the chemical reaction. For example, 3-trifluoromethyl-aniline is employed for synthesis of 4-chloro-3-methyl-7-trifluoromethyl-quinoline.

Andersag references:
1. Andersag, H. 1948. Antimalariamittel aus der Gruppe halogensubstituierter Chinolinverbindungen. Chem. Ber. 81:499-507.
2. Andersag, H., S. Breitner, and H. Jung. 1939. Deutsches Reichspatent (German) patent 683,692.
3. Andersag, H., S. Breitner, and H. Jung. March 4, 1941. Quinoline compound and process of making the same. Patent 2,233,970. . United States.

Synthesis of Pharmachin 128.

COMPOUNDS FOR TREATING PARASITIC DISEASE

CROSS REFERENCE TO RELATED APPLICATIONS

This is the U.S. National Stage of International Application No. PCT/US2009/064811, filed Nov. 17, 2009, which was published in English under PCT Article 21(2), which in turn claims the benefit of U.S. Provisional Application No. 61/199,653, filed on Nov. 18, 2008. The provisional application is incorporated herein in its entirety.

ACKNOWLEDGMENT OF GOVERNMENT SUPPORT

The United States Government may have certain rights to invention(s) disclosed herein as research that may be relevant to the development of the invention was funded by United States governmental grant funds from the United States Department of Veteran Affairs Medical Research Program.

FIELD

The compounds and composition disclosed herein relate to inhibiting parasitic disease, particularly malaria.

BACKGROUND

Malaria is a tropical disease, spread by mosquitoes from person to person, that exacts a devastating toll in endemic regions, especially Africa, where it claims 1 to 2 million lives each year. The deaths occur primarily among young children and pregnant women—vulnerable populations for whom therapeutic options are limited. These options are even more restricted in the current landscape of widespread drug resistance in the *Plasmodium* parasites that cause malaria. Together with an increasing incidence of malaria worldwide, there is an urgent and unmet need for new drugs to prevent and treat malaria, an infection that causes clinical disease manifestations in 300 to 500 million people each year.

Malaria is a worsening global health problem. The incidence of malaria continues to increase worldwide, due in part to the emergence of drug resistance but also due to global warming. Initially observed in the late 1950's and early 1960's in South America and Southeast Asia, chloroquine-resistant *Plasmodium* parasites that are associated with the most virulent form of malaria, cerebral malaria, have now spread to all malarious regions of the world. Varney et al. (1994) (1997) and others report a strong correlation between cerebral malaria and neuropsychiatric symptoms, such as poor dichotic listening, 'personality change', depression, and, in some cases, partial seizure-like symptoms. The tropical neuralnesia resulting from the legendary malarial fevers is well known in the endemic areas and has been documented throughout history.

Chloroquine replacement drugs are urgently needed to treat and prevent malaria. The endoperoxides, like artemisinin (derived from a Chinese herbal remedy extracted from the wormwood plant) are being used in other parts of the world for malaria therapy. However, the use of this remedy is limited by reports of ototoxicity and neurotoxic effects of the endoperoxides. More recently, severe reproductive toxicity in female rats has been reported in animals treated with artesunate and its active metabolite, dihydroartemisinin. These findings are mirrored in reports by others in several different animal models. While the great panacea for malaria therapy would be the development of a long-lasting vaccine, the recent failure of the SPf66 vaccine and unrealized potential of newer multi-component DNA vaccines, combine to indicate that a vaccine is a long way from reality. As a result, the need continues to exist in the medical field for the development of safe, inexpensive anti-parasitic agents, especially agents that are useful against multi-drug-resistant organisms such as *P. falciparum* and *P. vivax*.

SUMMARY

Disclosed herein are compounds according to formula I:

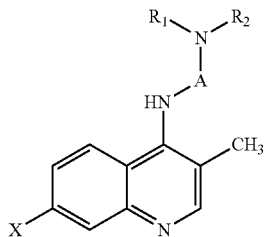

or a pharmaceutically acceptable salt thereof, wherein:
X is an electron-withdrawing group;
A is an optionally substituted alkanediyl or an optionally substituted cycloalkanediyl that includes 2 to 5 carbon atoms; and
$R_1$ and $R_2$ are each individually H, tert-butyl, isopropyl, ethyl, propyl, or an optionally substituted cycloalkyl, or $R_1$ and $R_2$ together form a substituted or unsubstituted heterocyclic ring system, provided that $R_1$ and $R_2$ are not both H or $R_1$ and $R_2$ are not both ethyl.

Also disclosed herein are compounds according to formula II;

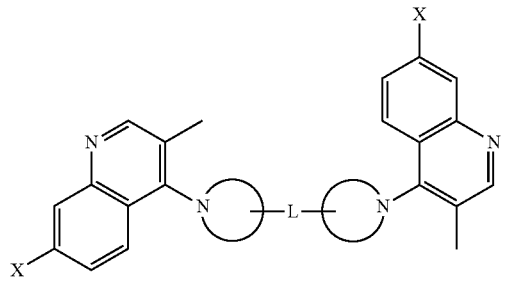

or a pharmaceutically acceptable salt thereof, wherein:
X is an electron-withdrawing group;
L is a linking group; and

represents a cyclic ring structure that optionally includes at least one additional heteroatom.

Also disclosed herein are compositions comprising a pharmacologically active amount of at least one compound of formula I, formula II, or a pharmaceutically acceptable salt thereof, and at least one pharmaceutically acceptable carrier.

According to another embodiment disclosed herein, there are provided methods for inhibiting a parasitic disease, especially drug-resistant malaria, in a subject comprising administering to the subject a therapeutically effective amount of a compound of formula I, formula II, or a pharmaceutically acceptable salt thereof.

A further embodiment disclosed herein concerns methods for inhibiting multidrug-resistant malaria in a subject comprising administering to the subject a therapeutically effective amount of a compound of formula IV:

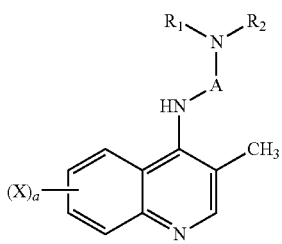

or a pharmaceutically acceptable salt thereof,
wherein X is an electron-withdrawing group;
a is 1 to 4;
A is —$CH_2$—$CH_2$— or —$CH_2$—$CH_2$—$CH_2$—; and
$R_1$ and $R_2$ are each individually H, a branched or unbranched alkyl having 1 to 6 carbon atoms, or a cycloalkyl.

Also disclosed herein is a compound according to formula V:

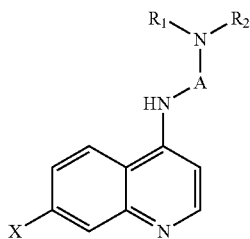

or a pharmaceutically acceptable salt thereof, wherein:
X is an electron-withdrawing group;
A is an optionally substituted alkanediyl or an optionally substituted cycloalkanediyl that includes 2 to 5 carbon atoms;
$R_1$ is H or an optionally substituted alkyl; and
$R_2$ is optionally substituted adamantyl.

BRIEF DESCRIPTION OF THE DRAWINGS

FIG. 1 depicts a generic synthesis scheme for 7-substituted, 4-aminoquinolines.

DETAILED DESCRIPTION

Figure 2:
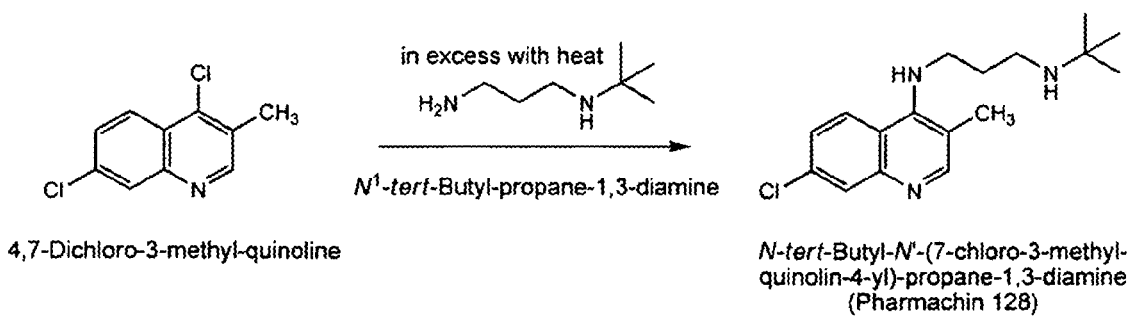
FIG. 2 depicts a synthesis for a specific novel compound disclosed herein.
Figure 3:
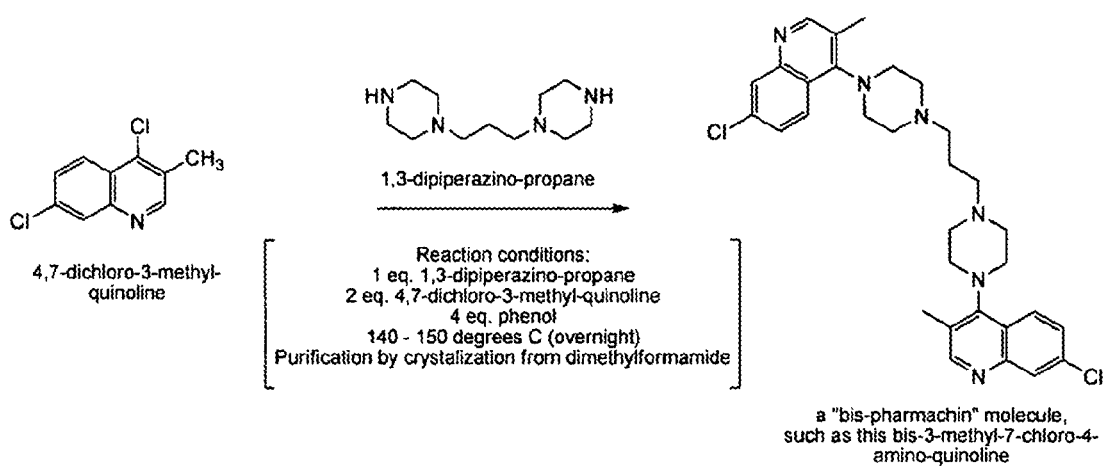
FIG. 3 depicts a generic synthesis scheme for additional compounds disclosed herein.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

Variables such as $R^1$, $R^2$, $R^3$, $R^4$, $R^5$, $R^6$, $R^7$, $R^8$, $R^9$, n, X and Y, used throughout the disclosure are the same variables as previously defined unless stated to the contrary.

The term "acyl" refers group of the formula RC(O)— wherein R is an organic group.

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

The term "aliphatic" is defined as including alkyl, alkenyl, alkynyl, halogenated alkyl and cycloalkyl groups as described above. A "lower aliphatic" group is a branched or unbranched aliphatic group having from 1 to 10 carbon atoms.

"Alkanediyl" or "cycloalkanediyl" refers to a divalent radical of the general formula —$C_nH_{2n}$— derived from aliphatic or cycloaliphatic hydrocarbons.

The term "alkenyl" refers to a hydrocarbon group of 2 to 24 carbon atoms and structural formula containing at least one carbon-carbon double bond.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, or carboxyl.

The term "alkyl amino" refers to alkyl groups as defined above where at least one hydrogen atom is replaced with an amino group.

The term "alkynyl" refers to a hydrocarbon group of 2 to 24 carbon atoms and a structural formula containing at least one carbon-carbon triple bond.

The term "alkoxy" refers to a straight, branched or cyclic hydrocarbon configuration and combinations thereof, including from 1 to 20 carbon atoms, preferably from 1 to 8 carbon atoms, more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, or heterocycloalkyl group as described above. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group described above.

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H) or —C(O)—N(R). An "aminocarbonyl" is inclusive of an amido group. A suitable aminocarbonyl group is acetamido.

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above. A suitable amido group is acetamido.

The term "aralkyl" refers to an aryl group having an alkyl group, as defined above, attached to the aryl group, as defined above. An example of an aralkyl group is a benzyl group.

The term "aryl" refers to any carbon-based aromatic group including, but not limited to, benzene, naphthalene, etc. The term "aryl" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

"Carboxyl" refers to a —COOH radical. Substituted carboxyl refers to —COOR where R is aliphatic, heteroaliphatic, alkyl, heteroalkyl, or a carboxylic acid or ester.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

"Derivative" refers to a compound or portion of a compound that is derived from or is theoretically derivable from a parent compound.

"Equipotency" refers to the capacity of the inventive compounds disclosed herein to inhibit the growth of parasites, especially drug-resistant *Plasmodium* parasites, with roughly the same power or capacity (e.g., with a range of 2 to 3-fold), regardless of the level of intrinsic resistance to chloroquine, quinine, or other antimalarial agents.

The terms "halogenated alkyl" or "haloalkyl group" refer to an alkyl group as defined above with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" (which is inclusive of "treating") refers to inhibiting the full development of a disease or condition, for example, in a subject who is at risk for a disease such as malaria. "Treatment" refers to a therapeutic intervention that ameliorates a sign or symptom of a disease or pathological condition after it has begun to develop. As used herein, the term "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease "Inhibiting" also refers to any quantitative or qualitative reduction including prevention of infection or complete killing of an invading organism, relative to a control. A "prophylactic" treatment is a treatment administered to a subject who does not exhibit signs of a disease or exhibits only early signs for the purpose of decreasing the risk of developing pathology. By the term "coadminister" is meant that each of at least two compounds be administered during a time frame wherein the respective periods of biological activity overlap. Thus, the term includes sequential as well as coextensive administration of two or more drug compounds.

"Invading" relates to a pathological activity of an organism against a healthy cell, a population of healthy cells, or whole organism.

"Multidrug-resistant" or "drug-resistant" refers to malaria, or the parasites causing malaria, that have developed resistance to treatment by at least one therapeutic agent historically administered to treat malaria. For example, there are multidrug-resistant strains of *Plasmodium falciparum* that harbor high-level resistance to chloroquine, quinine, mefloquine, pyrimethamine, sulfadoxine and atovaquone.

Optionally substituted groups, such as "optionally substituted alkyl," refers to groups, such as an alkyl group, that when substituted, have from 1-5 substituents, typically 1, 2 or 3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, halogen, optionally substituted heteroaryl, optionally substituted heterocyclyl, hydroxy, sulfonyl, thiol and thioalkoxy. In particular, optionally substituted alkyl groups include, by way of example, haloalkyl groups, such as fluoroalkyl groups, including, without limitation, trifluoromethyl groups.

"Optional" or "optionally" means that the subsequently described event or circumstance can but need not occur, and that the description includes instances where said event or circumstance occurs and instances where it does not.

The terms "pharmaceutically acceptable salt" or "pharmacologically acceptable salt" refers to salts prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

The term "pharmacologically active amount" relates to an amount of a compound that provides a detectable reduction in parasitic activity in vitro or in vivo, or diminishes the likelihood of emergence of drug resistance.

"Saturated or unsaturated" includes substituents saturated with hydrogens, substituents completely unsaturated with hydrogens and substituents partially saturated with hydrogens.

The term "subject" includes both human and veterinary subjects.

A "therapeutically effective amount" or "diagnostically effective amount" refers to a quantity of a specified agent sufficient to achieve a desired effect in a subject being treated with that agent. For example, this may be the amount of a compound disclosed herein useful in detecting or treating thyroid cancer in a subject. Ideally, a therapeutically effective amount or diagnostically effective amount of an agent is an amount sufficient to inhibit or treat the disease without causing a substantial cytotoxic effect in the subject. The therapeutically effective amount or diagnostically effective amount of an agent will be dependent on the subject being treated, the severity of the affliction, and the manner of administration of the therapeutic composition.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts Protective Groups in Organic Synthesis; 3rd Ed.; John Wiley & Sons, New York, 1999.

In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS—Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts Protective Groups in Organic Synthesis; 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

It is understood that substituents and substitution patterns of the compounds described herein can be selected by one of ordinary skill in the art to provide compounds that are chemically stable and that can be readily synthesized by techniques known in the art and further by the methods set forth in this disclosure. Reference will now be made in detail to the presently preferred compounds.

The following abbreviations are used herein:
$ED_{50}$—effective drug concentration required to decrease parasitemia by 50% relative to control, untreated animals;
FACS—fluorescence activated cells sorting/scanning;
Gavage—oral route of drug administration;
$IC_{50}$—drug concentration required to inhibit parasite growth by 50% relative to control values;
i.p.—intraperitoneal;
i.v.—intravenous;

IVTI—in vitro therapeutic index; calculated from the ratio of $IC_{50}$ value based on the cytotoxicity observed in the blastogenesis assay and the anti-malarial potency against the D6 strain (non-drug resistant, drug sensitive) of *P. falciparum*.

MSF—malaria specific fluorescence assay;

PRBC—parasitized red blood cell(s);

RFU—relative fluorescence units

Compounds

The inventive compounds disclosed herein represent clinically viable options for the treatment of malaria. In particular, the inventive compounds may exhibit equipotency against chloroquine sensitive and multidrug-resistant strains of *Plasmodium* parasites, offer enhanced efficacy in vivo, exhibit enhanced metabolic stability, and/or have a greatly diminished likelihood for the emergence of parasite drug resistance. The inventive compounds are referred to herein as "Pharmachins" or "pharmakins", however Pharmachins is the preferred spelling. Certain examples of the pharmachins are characterized by physical, chemical and pharmacological qualities that are highly desirable in any new antimalarial: molecular weight <500; logP value <5; stable salt formulation; and strong antiparasitic action in vitro and in vivo.

The inventive compounds disclosed herein should have a greatly diminished likelihood for emergence of drug resistance since there are two structural motifs built into the design of the compounds as a countermeasure to resistance. In particular, examples of the compounds disclosed herein may exhibit equipotency against multiquinoline-resistant *plasmodium* parasites including chloroquine-resistant parasites. The compounds disclosed herein are composite compounds that incorporate two independent structural features that independently circumvent chloroquine- and multiquinoline-resistance in the *Plasmodium* parasites. Although not bound by any theory, it is believed that a shorter alkyl chain length (e.g., ethyl or propyl) for the 4-position α,ω-diaminoalkane of the 4-aminoquinoline moiety combined with a t-butyl (or similar structure) moiety attached to the terminal amino group of the diaminoalkane should enhance metabolic stability and exhibit a diminished likelihood for the emergence of drug resistance. The 3-methyl substituent on the quinoline ring also circumvents chloroquine-resistance, but in a mechanistically independent manner as compared to the shorter alkyl side chain/t-butyl construct. Thus, the compounds disclosed herein combine both the 3-methyl group and the shorter alkyl side chain as a double-evasion mechanism against multidrug resistance together with the terminal t-butyl group to enhance metabolic stability.

In the compounds of formulas I-IV, X is an electron-withdrawing group that may enhance complexation to free heme, antiparasitic activity, and metabolic stability. For example, X may be halogen, halogenated alkyl, halogenated alkoxy, alkoxy, sulfonyl alkyl, sulfonyl halogenated alkyl, sulfamyl, $SF_5$, carboxyl or substituted carboxyl. In certain embodiments, X is halogen, particularly Cl. A is an alkanediyl, or cycloalkanediyl, that includes 2 to 5 carbon atoms, more particularly 2 or 3 carbon atoms. For example, A may be —$(CH_2)_n$— wherein n is 2 to 5, more particularly 2 or 3. In certain embodiments, A is a substituted alkanediyl wherein the substituent is hydroxyl, alkyl (particularly lower alkyl) or alkoxy (particularly an alkoxy containing 1 to 4 carbon atoms). For example, A may be —$CH_2$—CH(OH)—$CH_2$—, —$CH_2$—CH(alkyl, e.g., $CH_3$)—$CH_2$—, or —$CH_2$—CH(alkoxy, e.g., $OCH_3$)—$CH_2$—.

$R_1$ and $R_2$ in the compounds of formula I are each individually H, tert-butyl, isopropyl, ethyl, propyl or cycloalkyl (e.g., a cycloalkyl of 3 to 12 carbon atoms), or $R_1$ and $R_2$ together form a substituted or unsubstituted heterocylic ring system, provided that $R_1$ and $R_2$ are not both H or $R_1$ and $R_2$ are not both ethyl (in other words, only one of $R_1$ or $R_2$ can be H or ethyl). In certain embodiments, $R_1$ is H and $R_2$ is tert-butyl. In other embodiments, $R_1$ is H and $R_2$ is cyclopropyl. In another embodiment, $R_1$ is ethyl and $R_2$ is tert-butyl or cycloalkyl. In further embodiments, $R_1$ and $R_2$ together form a substituted or unsubstituted piperidinyl, substituted or unsubstituted pyrrolidinyl, or a substituted or unsubstituted piperazinyl. In an additional embodiment, $R_1$ is H, tert-butyl, isopropyl, ethyl, or propyl and $R_2$ is adamantyl, which $R_2$ may be optionally substituted with alkyl (particularly lower alkyl such as methyl), or alkoxy (particularly lower alkoxy such as methoxy).

In certain embodiments of the compound of formula I, A is an alkanediyl or cycloalkanediyl that includes 2 to 5 carbon atoms; and $R_1$ and $R_2$ are each individually H, tert-butyl, isopropyl, or cycloalkyl, or $R_1$ and $R_2$ together form a substituted or unsubstituted heterocyclic ring system, provided that $R_1$ and $R_2$ are not both H.

$R_1$ and $R_2$ in the compounds of formula IV are each individually H, an alkyl having 1 to 6 carbon atoms, or a cycloalkyl. In certain examples, $R_1$ and $R_2$ in the compounds of formula IV are each individually H, tert-butyl, isopropyl or cycloalkyl. In one example, $R_1$ is H and $R_2$ is adamantyl, which may be optionally substituted with alkyl (particularly lower alkyl such as methyl), or alkoxy (particularly lower alkoxy such as methoxy).

In the compounds of formula II, L is a linking group that may be an alkanediyl, or cycloalkanediyl, that includes 2 to 5 carbon atoms, more particularly 2 or 3 carbon atoms. For example, A may be —$(CH_2)_n$— wherein n is 2 to 5, more particularly 2 or 3.

The structure

represents a cyclic ring structure that optionally includes at least one additional heteroatom. The cyclic ring structure may be a 4, 5 or 6-member ring. The additional heteroatom may be N or O. Illustrative ring structures include pyrrolidinyl, pyridinyl, piperidinyl, or piperazinyl. The linking group L may be attached at any position of the cyclic ring structure.

In the compounds of formula V, $R_1$ is H or an optionally substituted alkyl (particularly a lower alkyl such as methyl, ethyl, propyl, or tert-butyl); and $R_2$ is optionally substituted adamantyl. In certain embodiments, the adamantyl of $R_2$ is not substituted.

According to a preferred embodiment, the compounds have a structure represented by formula III:

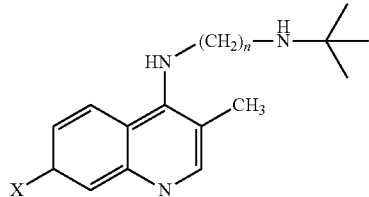

wherein n is 2 or 3.

Illustrative compounds of formula I include:

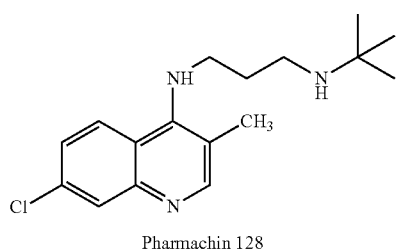

Pharmachin 128

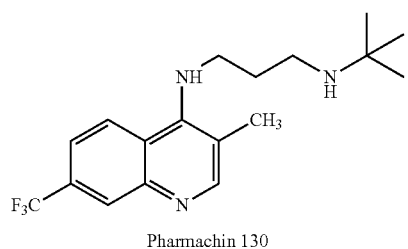

Pharmachin 130

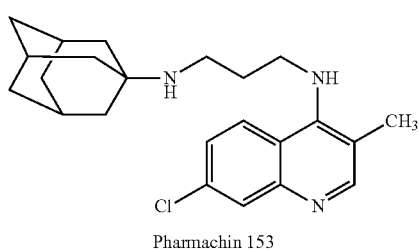

Pharmachin 153

Illustrative compounds of formula II include:

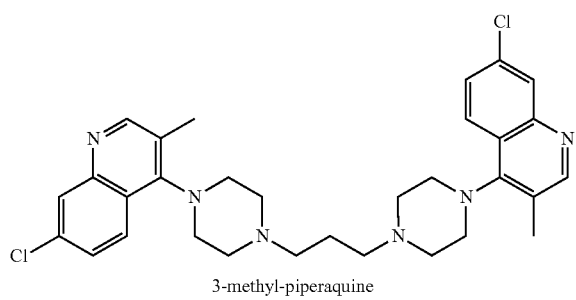 [SMILES: Cc1cnc2cc(Cl)ccc2c1N1CCN(CCCN2CCN(c3c(C)cnc4cc(Cl)ccc34)CC2)CC1]

3-methyl-piperaquine

Illustrative compounds of formula V include:

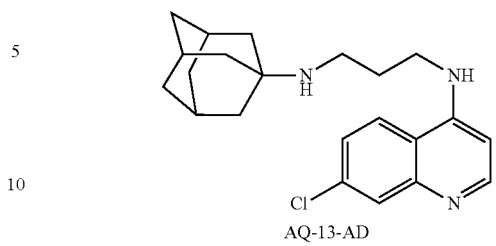

AQ-13-AD

FIG. 1 depicts a general scheme for synthesizing the compounds disclosed herein.

Composition and Methods

The compounds and pharmaceutical compositions disclosed herein can be used for inhibiting or preventing parasitic diseases. For example, human or animal parasitic diseases include malaria, toxoplasmosis, amebiasis, giardiasis, leishmaniasis, trypanosomiasis, and coccidiosis, caused by organisms such as *Toxoplasma* sp., *Eimeria* sp., *Babesia bovis*, *Theileria* sp., and also includes infections by helminths, such as ascaris, schistosomes and filarial worms. The compounds and compositions are also effective in the inhibition of fungal pathogens including *Pneumocystis carinii*, *Aspergillus fumigatus*, and others.

In particular embodiments, the parasitic diseases may be caused by parasites that cause malaria. Particular species of parasites that are included within this group include all species that are capable of causing human or animal infection. Illustrative species include *Plasmodium falciparum*, *Plasmodium vivax*, *Plasmodium ovale*, *Plasmodium knowlesi*, and *Plasmodium malariae*. The novel compounds and compositions disclosed herein are particularly useful for inhibiting drug-resistant malaria such as chloroquine-resistant malaria or multidrug-resistant malaria that is caused by organisms harboring resistance to chloroquine, quinine, mefloquine, pyrimethamine, dapsone, and atovaquone. One embodiment disclosed herein includes administering at least one of the compounds disclosed herein to a subject determined to be in need of treatment for multidrug-resistant malaria.

In further embodiments, the inventive compounds disclosed herein may be co-administered with another pharmaceutically active compound. For example, the compounds may be co-administered with quinine, chloroquine, atovaquone, proguanil, primaquine, amodiaquine, mefloquine, piperaquine, artemisinin, artesunate, methylene blue, pyrimethamine, sulfadoxine, artemether-lumefantrine (Coartem®), dapsone-chlorproguanil (LAPDAP®), artesunate, quinidine, clopidol, pyridine/pyridinol analogs, 4(1H)-quinolone analogs, dihydroartemisinin, a mixture of atovaquone and proguanil, an endoperoxide, an acridone as disclosed in WO 2008/064011 (which is incorporated herein by reference in its entirety) or any combination of these.

The compounds disclosed herein may be included in pharmaceutical compositions (including therapeutic and prophylactic formulations), typically combined together with one or more pharmaceutically acceptable vehicles or carriers and, optionally, other therapeutic ingredients (for example, antibiotics, anti-inflammatories, or drugs that are used to reduce pruritus such as an antihistamine). The compositions disclosed herein may be advantageously combined and/or used in combination with other antimalarial agents as described above.

Such pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

Typical subjects intended for treatment with the compositions and methods of the present disclosure include humans, as well as non-human primates and other animals. To identify subjects for prophylaxis or treatment according to the methods of the disclosure, accepted screening methods are employed to determine risk factors associated with a parasitic infection to determine the status of an existing disease or condition in a subject. These screening methods include, for example, preparation of a blood smear from an individual suspected of having malaria. The blood smear is then fixed in methanol and stained with Giemsa and examined microscopically for the presence of *Plasmodium* infected red blood cells. These and other routine methods allow the clinician to select patients in need of therapy using the methods and pharmaceutical compositions of the disclosure.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, transepidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the conjugates described herein. In one example, this component is formulated in a pharmaceutical preparation for delivery to a subject. The conjugate is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

EXAMPLES

Chemical Synthesis of 7-Chloro-3-Methyl-4-(3-t-butylaminopropylamino)-quinoline (Pharmachin 128) (see FIG. 2)

Pharmachin 128 was obtained by the procedure applied by Andersag, H. 1948, Antimalariamittel aus der Gruppe halogensubstituierter Chinolinverbindungen. Chem. Ber. 81:499-507, and described by him in patents in Deutsches Reichspatent 683,692 (1939) and U.S. Pat. No. 2,233,970 for the synthesis of sontochin.

Method: 4,7-Dichloro-3-methylquinoline (0.50 g, 2.4 mmol) and 3-(t-butylamino)-aminopropane 2 g, 15.4 mmol) are refluxed for 20 hours, and the excess amine is then distilled off (high vacuum, 130° C.) and the residue, dissolved in a few milliliters of methanol, treated with 100 ml of 2 N NaOH. The united extracts (2×50 ml ethyl acetate) are washed with water (10 ml) and brought to dryness (vacuum). The residue is chromatographed on a column of Kieselgel Merck (5 cm i.d.×3 cm height) with a mixture of 2:1 triethylamine—hexane. The pure compound elutes early on. After evaporation (vacuum) and re-crystallization from triethylamine 0.44 g of pale yellow, large crystals remain, m.p.=117° C. $^1$H-n.m.r. spectrum (CDCl$_3$, 400 MHz)): $\delta_2$=8.40 p.p.m., s, 1H; $\delta_{CH3(3)}$=2.38, s, 3H; $\delta_5$=8.01, d, J=9.07 Hz, 1H; $\delta_6$=7.30, d-d, J=9.07, J=2.23, 1H; $\delta_8$=7.91, d, J=2.22. Amine side-chain position 4 (Ring-N(1)-C(1)-C(2)-C(3)-N (3)): $\delta_{CH2(1)}$=3.72, t (br.), 2H; $\delta_{CH2(2)}$=1.61, p, J=5.9, 2 H; $\delta_{CH2(3)}$=2.84, t (distorted), 2H; $\delta_{C(CH3)3}$=1.14, s, 9H; $\delta_{NH}$=6.14, s (br.), 1.0H. G.c.-m.s.: M$^+$=305, 307 in the ratio 3:1=M($^{35}$Cl)$^+$: M($^{37}$Cl)$^+$.

7-Chloro-3-Methyl-4-(3-(diethylamino)-propylamino)-Quinoline, 7-Chloro-3-Methyl-4-(3-(diethylamino)-ethylamino)-Quinoline, 6-Chloro-3-Methyl-4-(3-t-butylaminopropylamino)-Quinoline, 5.7-Difluoro-3-Methyl-4-(3-t-butylaminpropyl-amino)-Quinoline, 7-Chloro-3-Ethyl-4-(3-(t-butylylamino)-propylamino)-Quinoline and 7-Trifluoromethyl-3-Methyl-4-(3-t-butylaminopropylamino)-Quinoline were similarly obtained.

Chemical Synthesis of 7-Chloro-(3-adamantylamino)-aminopropylquinoline 4.7-dichloroquinoline (0.29 g), 1 g of phenol and 0.6 g of impure (containing 1-aminoadamantane) 3-adamantylaminopropylamine were heated at 120° C. for 3 hours. By g.c.-m.s. analysis it was found that the mixture contained besides the aimed—at product, 1-aminoadamantane, some 4.7-dichloroquinoline and a product which is by its mass spectrum 7-chloro-4-adamantylaminoquinoline (M$^+$=312.5). The mixture was dissolved in several ml of methanol, poured into 50 ml of 10% KOH and extracted with t-butyl methyl ether (2×50 ml). The combined extracts were brought to dryness, the residue dissolved in a mixture of N(C$_2$H$_5$)$_3$, little (CH$_3$)$_3$COCH$_3$ and some methanol, transferred to a column (5 cm. diameter, Kieselgel, wetted with N(C$_2$H$_5$)$_3$: (CH$_3$)$_3$OCH$_3$: CH$_3$OH=125:75:5 (by volume) and eluted with 205 ml of this solvent. The solvent was changed to N(C$_2$H$_5$)$_3$: (CH$_3$)$_3$OCH$_3$:CH$_3$OH=100:100:10 (by volume), and the product together with M$^+$=151 (adamantylamine) was eluted, +another by-product (by g.c.-m.s. perhaps 7-chloroquinolone, which was not in the crude product prior to base-treatment). After re-elution (30 g Kieselgel, N(C$_2$H$_5$)$_3$: CH$_3$OH=200:5, fraction collection and their g.c.-m.s. analysis), 33 mg of pure 7-chloro-(3-adamantylamino)-aminopropylquinoline was obtained as a white solid. Yield=6% of theory. G.c.-m.s. (DB5-column, 30 m, injection block temperature=250° C., t0=150° C./2 min, then 11° C./min.→280° C., Rt=24.05 min.): M($^{35}$Cl, $^{37}$Cl)$^+$=369 (24%), 371 (9%), 135, C$_{10}$H$_{15}^+$, (100%).

$^1$H-n.m.r. spectrum (400 MHz, CDCl$_3$, Si(CH$_3$)$_4$=0): $\delta_2$=8.49, d, J=5.40 Hz, 1H, $\delta_3$=28, d, J=5.40, 1H; $\delta_5$=7.84, d=J=9.0, 1H; $\delta_6$=7.32, d-d, J=8.97, J=2.17 Hz; $\delta_8$=7.92, d, 2.14, 1H. $\delta_{NH}$=8.2 s, br., 0.84H. Propylchain: $\delta_{1,3}$=3.39, dist. t, 2H; $\delta_{1,3}$=2.93, distorted t, 2H; $\delta_2$=1.9, symm m, 2H. Adamantyl group: $\delta$=2.1, s, br, 3H(CH); $\delta$=1.55-1.73, sev. br. features, 12H(CH$_2$).

Parasite culture and drug susceptibility assays: Four different laboratory strains of P. falciparum were cultured in human erythrocytes by standard methods under a low oxygen atmosphere (5% O$_2$, 5% CO$_2$, 90% N$_2$) in an environmental chamber (Trager, W., and J. Jensen. 1976. Human malaria parasites in continuous culture. Science 193:673-675). The culture medium was RPMI 1640, supplemented with 25 mM Hepes buffer, 25 mg/liter gentamicin sulfate, 45 mg/liter hypoxanthine, 10 mM glucose, 2 mM glutamine, and 0.5% Albumax II. The parasites were maintained in fresh human erythrocytes suspended at a 2% hematocrit in complete medium at 37° C. Stock cultures were sub-passaged every 3 to 4 days by transfer of infected red cells to a flask containing complete medium and uninfected erythrocytes.

In vitro antimalarial activity of the test compounds was assessed by a fluorescence-based method described previously by Smilkstein M., N. Sriwilaijaroen, J. X. Kelly, P. Wilairat, and M. Riscoe. 2004. Simple and inexpensive fluorescence-based technique for high-throughput antimalarial drug screening. *Antimicrob Agents Chemother* 48:1803-6. The experiments were set up in triplicate in 96 well plates with two-fold dilutions of each compound across the plate in a total volume of 100 µl and at a final red blood cell concentration of 2% (v/v). Stock solutions of each compound were prepared by dissolving in DMSO at 10 mM. The dilution series was initiated at a concentration of 1 µM and the experiment was repeated beginning with a lower initial concentration for those compounds in which the IC$_{50}$ value was below 10 nM. In every case, an additional determination was performed to ensure bracketing of the IC$_{50}$ value by at least an order of magnitude. Automated pipeting and dilution was carried out by a programmable Precision 2000 robotic station (Bio-Tek, Winooski, Vt.). An initial parasitemia of 0.2% was attained by addition of normal uninfected red cells to a stock culture of asynchronous parasite infected red cells (PRBC).

The plates were incubated for 72 hrs at 37° C. in an atmosphere of 5% $CO_2$, 5% $O_2$, and 90% $N_2$. After this period the SyBr Green I dye-detergent mixture (100 µl) was added and the plates were incubated at room temperature for an hour in the dark and then placed in a 96-well fluorescence plate reader (Gemini-EM, Molecular Diagnostics) for analysis with excitation and emission wavelength bands centered at 497 and 520 nm, respectively. The fluorescence readings were plotted against the logarithm of the drug concentration and curve fitting by nonlinear regression analysis (GraphPad Prism software) yielded the drug concentration that produced 50% of the observed decline from the maximum readings in the drug-free control wells ($IC_{50}$). The results are shown below in Table 1.

TABLE 1

Antiplasmodial $IC_{50}$ values* (nM) for chloroquine, sontochin and pharmachin compounds against chloroquine sensitive (D6) and multidrug-resistant (Dd2, Tm90.C2B, and 7G8) strains of Plasmodium falciparum.

| Compound name or # | D6 strain | Dd2 strain | Tm90.C2B strain | 7G8 strain |
|---|---|---|---|---|
| Chloroquine | 11.2 | 160 | 144 | 55 |
| Quinine | 19 | 87 | 96 | 29.5 |
| Atovaquone | 0.1 | 0.1 | 7,700 | NT |
| Sontochin | 8.6 | 11.3 | 13.8 | NT |
| AQ-13 | 7.2 | 8.1 | NT | 12.0 |
| Pharmachin 112 | 12.8 | 17.7 | 16.6 | NT |
| Pharmachin 127 | 14.1 | 17.8 | 18.3 | NT |
| Pharmachin 128 | 6.2 | 11.6 | 12.0 | 11.3 |
| Pharmachin 129 | 94.8 | 127 | NT | NT |
| Pharmachin 130 | 15.0 | 21.9 | NT | 25.9 |
| Pharmachin 131 | 122 | 340 | 302 | NT |
| Pharmachin 137 | 133 | 233 | NT | 273 |
| AQ-13-AD | 3.8 | 4.2 | 4.9 | NT |
| 3-methyl-piperaquine | 4.6 | 6.5 | NT | 9.5 |

*$IC_{50}$ values were determined by the fluorescence based SyBr Green assay first described by Dr. Martin Smilkstein et al. (2004). Values are the mean of at least two experiments, each performed in triplicate, and did not vary by greater than 15% between experiments.

NT = not tested.

Note that P. falciparum strains Dd2, Tm90.C2B, and 7G8 are resistant to chloroquine and quinine.

AQ-13 is a compound disclosed in De et al, Aminoquinolines that Circumvent Resistance in Plasmodium falciparum In Vitro, Am. J. Trop. Med. Hyg. 55(6), 1996, pp. 579-583 and has the structure:

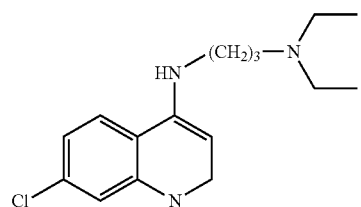

Additional compounds of Table 1 have the structures:

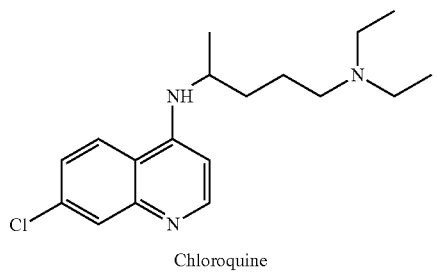

Chloroquine

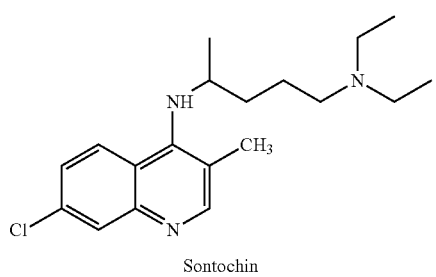

Sontochin

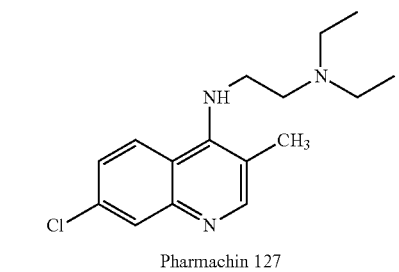

Pharmachin 127

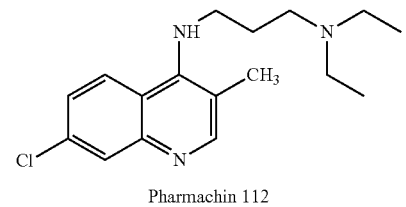

Pharmachin 112

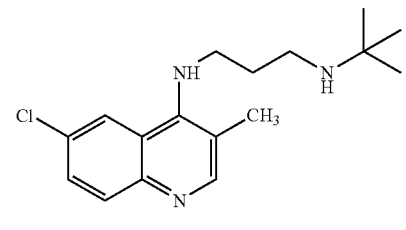

Pharmachin 129

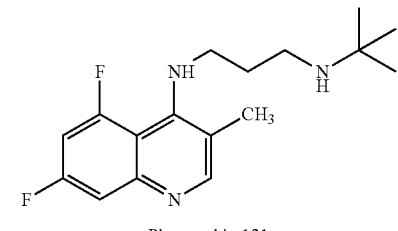

Pharmachin 131

-continued

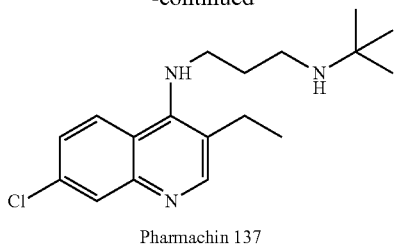

Pharmachin 137

Table 1 shows the $IC_{50}$ values of several standard antimalarial agents in comparison to sontochin (also known as 3-methyl-chloroquine and SN-6911) and a number of 3-methyl-4-aminoquinoline derivatives known as Pharmachins As shown, the D6 strain of *P. falciparum* is sensitive to the antiplasmodial action of chloroquine but strains Dd2, Tm90.C2B, and 7G8 are resistant to the drug. The Dd2 and Tm90.C2B strains also exhibit a high level of resistance to quinine while the latter also harbors resistance to atovaquone, a hydroxynaphthoquinone. It is evident that sontochin, which differs from chloroquine only in the 3-position methyl group, retains activity against the drug resistant strains of *P. falciparum* with $IC_{50}$ values ranging from 8.6 to 13.8 nM. AQ-13, a short-chain analog of chloroquine, also shows a high level of antiplasmodial activity against all tested drug resistant strains. The pharmachin analogs, containing both the 3-methyl substituent and the short chain (propyl) extending from the 4-amino position, show a range of inhibitory activities with pharmachin 128 as superior to all others with $IC_{50}$ values ranging from 6.2 to 12 nM against all 4 *P. falciparum* strains regardless of their pharmaco-resistance profiles.

In summary of our in vitro findings, pharmachin 128 is a composite molecule in which we have incorporated two independent structural features which independently circumvent chloroquine- and multiquinoline resistance in the *Plasmodium* parasite that causes malaria in humans. The novel co-existence of these two structural features in a single molecule should greatly diminish the likelihood for emergence of resistant strains and ensure that the drug will enjoy a long useful clinical life in the field for treatment and prevention of malaria. Consider, for example, if one in $10^9$ parasites is resistant to the short chain feature of pharmachin 128 and one in $10^{13}$ parasites is resistant to the 3-methyl feature of the pharmachin 128 (assuming that a single mutation could not confer resistance to both features—a reasonable assumption given the apparent lack of cross resistance) then only one in $10^{22}$ parasites (i.e., $10^9 \times 10^{13}$) would be simultaneously resistant to both structural features. Given these calculations that are based on logical assumptions of resistance frequencies to antiparasitic agents together with the fact that a biomass of $10^{13}$ parasites in a single patient is impossible, then the incidence of a parasite emerging with simultaneous resistance to both structural features (i.e., 3-alkyl moiety and short chain) could occur once in every $10^{12}$ treatments (i.e., estimated to be less once per century).

Efficacy of compounds in vivo. These experiments were designed based on a modified "Thompson test" as described in Ager, A. J. 1984, Rodent malaria models, vol. 68/I. Springer-Verlag, Berlin. This test monitors suppression of patent infection in female CF1 Swiss albino mice ($\approx$20 gm). A test begins with the inoculation of *Plasmodium yoelii* parasitized erythrocytes (100,000 to 500,000; obtained from a donor animal) on the first day of the experiment (D0). After 24 hours, the standard agents or pharmachin compounds were administered by gavage at daily intervals for three successive days. Initially the test compounds were examined at 128 mg/kg/day, 64 mg/kg/day, 16 mg/kg/day and 4 mg/kg/day and including a vehicle-only control. After completion of drug treatment, the animals were weighed and a blood sample was collected for the determination of parasite burden beginning on the day after the final dose has been administered (usually D5). The parasite burden in each blood sample was determined by direct microscopic analysis of methanol-fixed, Giemsa-stained blood smears. Drug activity was recorded as % suppression of parasite burden relative to drug-free controls. Based on the initial screening results, a tighter range of dosages to determine the $ED_{50}$ value for each drug was selected. The $ED_{50}$ value is the dosage of drug required to achieve a 50% reduction in parasitemia relative to the vehicle-only control; non-linear regression analysis was employed to generate $ED_{50}$s from the accumulated data.

Based on the observation that pharmachin 128 is equipotent against the chloroquine sensitive D6 strain of *P. falciparum* as well as the multidrug resistant strains in vitro, this compound was selected for further study. An in vivo experiment was performed to compare the efficacy of pharmachin 128 to pharmachin 112 in the *P. yoelii* system described above, with chloroquine as a positive control. Mice were split into groups of 3 each and animals were dosed by gavage at the following dosages: 128 mg/kg; 64 mg/kg; 16 mg/kg; and 3 mg/kg. The drugs were administered daily for 3 days and blood smears were taken on the $4^{th}$ day. The pharmachins (each in the free base form) were prepared in miglyol 812 whilst chloroquine was prepared in water. $ED_{50}$ values were calculated by graphical analysis of the dose-response effect. Pharmachin 112 exhibited an $ED_{50}$ value of 6.5 mg/kg/day while Pharmachin 128 yielded an $ED_{50}$ of 2.5 mg/kg/day, which was comparable to the efficacy of chloroquine ($ED_{50}$ 2.4 mg/kg/day) in this model system. All of the animals in this study gained weight over the course of experimentation equal to that in the drug-free control group indicating that the drugs were not toxic over the tested dosage range.

Follow-up studies with Pharmachin 128 were preformed in mice infected with *P. berghei* (ANKA/GFP) using a modified 4 day test. Animals (CF1) were inoculated (iv) with 1 million infected red blood cells, obtained from donor animals, and then randomly sorted into groups of 5 mice each. Once parasitemia had risen to =1-2 percent (typically 48 hrs after inoculation), drug administration commenced.

In this set of experiments Pharmachin 128 was administered daily by gavage as the citrate salt dissolved in water (100 µl) for each of 4 days. Dosing was set at 64, 16, 4, 2, and 1 mg/kg/day, respectively, and including a no drug control. Blood films were prepared on the $5^{th}$ day (i.e., the day after the final drug dose), fixed in methanol, stained with Giemsa, and viewed microscopically to assess parasitemia. Upon examination of the Giemsa smears it was revealed that while control animals exhibited parasitemias of =60%, bloodstream parasites were completely cleared by administration of 16 mg/kg and 64 mg/kg/day Pharmachin 128. While the latter group of animals remained aparasitemic for the full 30-day examination period (scored as cures), 2 of the 5 animals in the 16 mg/kg group recrudesced 2 weeks after the last dose. $ED_{50}$ (2.7 mg/kg/day) and $ED_{90}$ (4.7 mg/kg/day) values were calculated for Pharmachin 128 in treating *P. berghei* in this test system yielding values that mirror published reports for chloroquine against this same species and strain (O'Neil, et al., 2009, O'Neill, et al., 2009).

Taken together, our results show that pharmachins retain their antiplasmodial activity against multidrug-resistant *Plasmodium falciparum* strains that infect humans and they are efficacious in vivo in a mouse model patent malaria infection.

Moreover, compounds such as Pharmachin 128 appear to be just as active and efficacious as chloroquine in this system which serves to highlight their potential to replace chloroquine as the standard of antimalarial therapy.

In view of the many possible embodiments to which the principles of the disclosed compounds and methods may be applied, it should be recognized that the illustrated embodiments are only examples and should not be taken as limiting the scope of the invention.

What is claimed is:

1. A compound according to formula I:

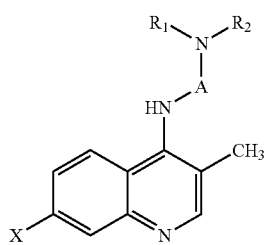

or a pharmaceutically acceptable salt thereof, wherein:
X is an electron-withdrawing group;
A is an optionally substituted alkanediyl or an optionally substituted cycloalkanediyl that includes 2 to 5 carbon atoms; and
$R_1$ and $R_2$ are each individually H, tert-butyl, isopropyl, ethyl, propyl, or optionally substituted cycloalkyl, or $R_1$ and $R_2$ together form a substituted or unsubstituted heterocyclic ring system, provided that $R_1$ and $R_2$ are not both H or $R_1$ and $R_2$ are not both ethyl; or a compound according to formula II:

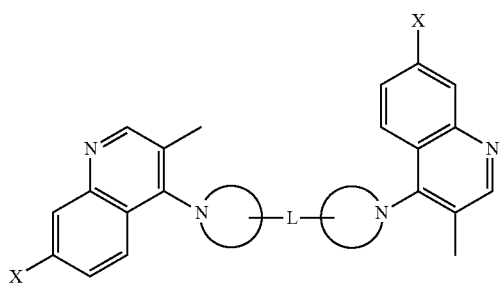

or a pharmaceutically acceptable salt thereof, wherein:
X is an electron-withdrawing group;
L is a linking group; and

represents a cyclic ring structure that optionally includes at least one additional heteroatom.

2. The compound of claim 1, wherein X is halogen, halogenated alkyl, halogenated alkoxy, alkoxy, sulfonyl alkyl, sulfonyl halogenated alkyl, sulfamyl, $SF_5$, carboxyl or substituted carboxyl.

3. The compound of claim 2, wherein X is Cl.

4. The compound of claim 1, wherein A is —(CH$_2$)$_n$— wherein n is 2 or 3.

5. The compound of claim 1, wherein $R_1$ is H and $R_2$ is tert-butyl.

6. The compound of claim 1, wherein $R_1$ and $R_2$ together form a substituted or unsubstituted piperidinyl, substituted or unsubstituted pyrrolidinyl, or a substituted or unsubstituted piperazinyl.

7. The compound of claim 1, wherein the compound has a structure represented by formula III:

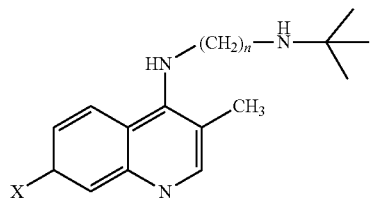

wherein n is 2 or 3.

8. The compound of claim 1, wherein L is an alkanediyl or cycloalkanediyl that includes 2 to 5 carbon atoms.

9. The compound of claim 1, wherein

represents a 4, 5 or 6-member ring, and the optional additional heteroatom is N or O.

10. The compound of claim 1, wherein the compound has the structure:

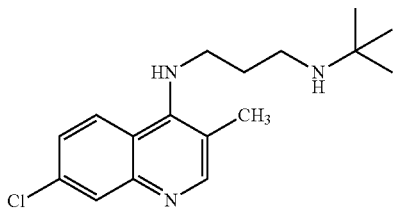

11. The compound of claim 1, wherein the compound has the structure:

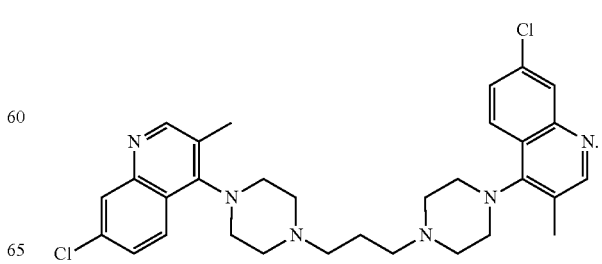

12. The compound of claim 1, wherein the compound has the structure:

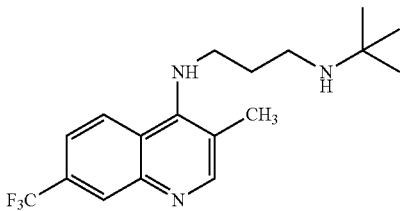

13. The compound of claim 1, wherein the compound exhibits equipotency against chloroquine-resistant and multidrug-resistant strains of *Plasmodium* parasites.

14. The compound of claim 1, wherein A is an alkanediyl or cycloalkanediyl that includes 2 to 5 carbon atoms; and $R_1$ and $R_2$ are each individually H, tert-butyl, isopropyl, or cycloalkyl.

15. The compound of claim 1, wherein A is a substituted alkanediyl wherein the substituent is hydroxyl, alkyl or alkoxy.

16. The compound of claim 1, wherein $R_1$ is H and $R_2$ is optionally substituted adamantyl.

17. The compound of claim 1, wherein $R_1$ is H and $R_2$ is adamantyl.

18. The compound of claim 1, wherein the compound has the structure:

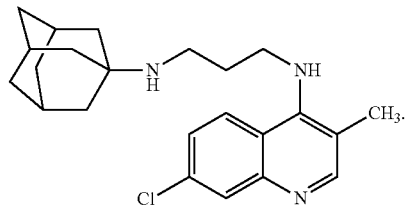 [SMILES: Cc1cnc2cc(Cl)ccc2c1NCCCNC12CC3CC(CC(C3)C1)C2]

19. A compound according to formula V:

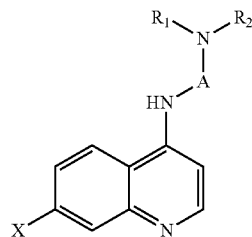

or a pharmaceutically acceptable salt thereof, wherein:
X is an electron-withdrawing group;
A is an optionally substituted alkanediyl or an optionally substituted cycloalkanediyl that includes 2 to 5 carbon atoms;
$R_1$ is H or an optionally substituted alkyl; and
$R_2$ is optionally substituted adamantyl.

20. The compound of claim 19, wherein X is halogen, halogenated alkyl, halogenated alkoxy, alkoxy, sulfonyl alkyl, sulfonyl halogenated alkyl, sulfamyl, $SF_5$, carboxyl or substituted carboxyl.

21. The compound of claim 19, wherein X is Cl.

22. The compound of claim 19, wherein A is $-(CH_2)_n-$ wherein n is 2 or 3.

23. The compound of claim 19, wherein the compound has the structure:

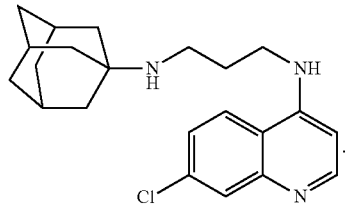 [SMILES: Clc1ccc2c(NCCCNC34CC5CC(CC(C5)C3)C4)ccnc2c1]

24. The compound of claim 1, wherein the pharmaceutically acceptable salt is a citrate.

25. A composition comprising a pharmacologically active amount of at least one compound of claim 1 or a pharmaceutically acceptable salt thereof, and at least one pharmaceutically acceptable carrier.

26. A method for inhibiting a parasitic disease in a subject comprising administering to the subject a therapeutically effective amount of a compound of claim 1 or a pharmaceutically acceptable salt thereof.

27. The method of claim 26, wherein the parasitic disease is malaria.

28. The method of claim 27, wherein the malaria is multidrug-resistant malaria.

29. The method of claim 27, wherein the parasitic disease is chloroquine-resistant malaria.

30. The method of claim 27, wherein the compound exhibits equipotency against chloroquine-resistant and multidrug-resistant strains of *Plasmodium* parasites.

31. The method of claim 26, further comprising co-administering the compound with at least one other antimalarial agent.

32. The method of claim 26, wherein the method comprises prophylactic treating the subject against chloroquine-resistant or multidrug-resistant malaria.

33. A method for inhibiting multidrug-resistant malaria in a subject comprising administering to the subject a therapeutically effective amount of a compound of formula IV, or a pharmaceutically acceptable salt thereof:

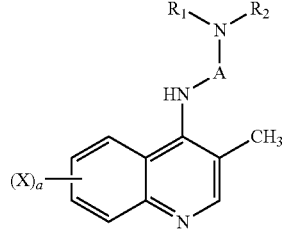

wherein X is an electron-withdrawing group;
a is 1 to 4;
A is $-CH_2-CH_2-$ or $CH_2-CH_2-CH_2-$; and
$R_1$ and $R_2$ are each individually H, a branched or unbranched alkyl having 1 to 6 carbon atoms, or a cycloalkyl.

34. A composition comprising a pharmacologically active amount of at least one compound of claim 19 or a pharmaceutically acceptable salt thereof, and at least one pharmaceutically acceptable carrier.

35. A method for inhibiting a parasitic disease in a subject comprising administering to the subject a therapeutically effective amount of a compound of claim 19 or a pharmaceutically acceptable salt thereof.

* * * * *